(12) United States Patent
Lian et al.

(10) Patent No.: US 8,843,198 B2
(45) Date of Patent: Sep. 23, 2014

(54) APPARATUS AND METHOD TO OPTIMIZE PACING PARAMETERS

(75) Inventors: Jie Lian, Beaverton, OR (US); Volker Lang, Berlin (DE); Hannes Kraetschmer, West Linn, OR (US); Dirk Muessig, West Linn, OR (US)

(73) Assignee: Biotronik SE & Co. KG, Berlin (DE)

( * ) Notice: Subject to any disclaimer, the term of this patent is extended or adjusted under 35 U.S.C. 154(b) by 115 days.

(21) Appl. No.: 13/603,418

(22) Filed: Sep. 5, 2012

(65) Prior Publication Data

US 2013/0079839 A1    Mar. 28, 2013

Related U.S. Application Data

(60) Provisional application No. 61/538,156, filed on Sep. 23, 2011.

(51) Int. Cl.
| | |
|---|---|
| *A61N 1/368* | (2006.01) |
| *A61B 5/04* | (2006.01) |
| *A61N 1/365* | (2006.01) |
| *A61N 1/362* | (2006.01) |
| *A61B 5/0402* | (2006.01) |

(52) U.S. Cl.
CPC .......... *A61N 1/3627* (2013.01); *A61N 1/36521* (2013.01); *A61N 1/3682* (2013.01); *A61B 5/0402* (2013.01); *A61N 1/3684* (2013.01); *A61N 1/3686* (2013.01)

USPC .............................................. 607/23; 600/514

(58) Field of Classification Search
USPC .............................. 600/508, 514, 523; 607/23
See application file for complete search history.

(56) References Cited

U.S. PATENT DOCUMENTS

| | | | |
|---|---|---|---|
| 2006/0106322 A1* | 5/2006 | Arand et al. ................... | 600/514 |
| 2008/0288013 A1* | 11/2008 | Schecter ......................... | 607/23 |
| 2009/0024045 A1* | 1/2009 | Prakash et al. ................ | 600/523 |

* cited by examiner

*Primary Examiner* — Carl H Layno
*Assistant Examiner* — Jon Eric C Morales
(74) *Attorney, Agent, or Firm* — ARC IP Law, PC; Joseph J. Mayo

(57) ABSTRACT

The present disclosure refers to a heart stimulator comprising a stimulation control unit, a stimulation unit, an impedance measurement unit and an impedance evaluation unit. The stimulation control unit is operatively connected to the stimulation unit to control timing of stimulation pulses by said stimulation unit. The impedance measurement unit is configured to determine an impedance signal reflecting intracardiac impedance. The impedance evaluation unit is operatively connected to the impedance measurement unit and to the stimulation control unit and is configured to evaluate the impedance signal so as to determine an isovolumic contraction time, an isovolumic relaxation time, an ejection time and a filling time from said impedance signal. The stimulation control unit is further configured to control timing of stimulation pulses depending on a performance index.

16 Claims, 7 Drawing Sheets

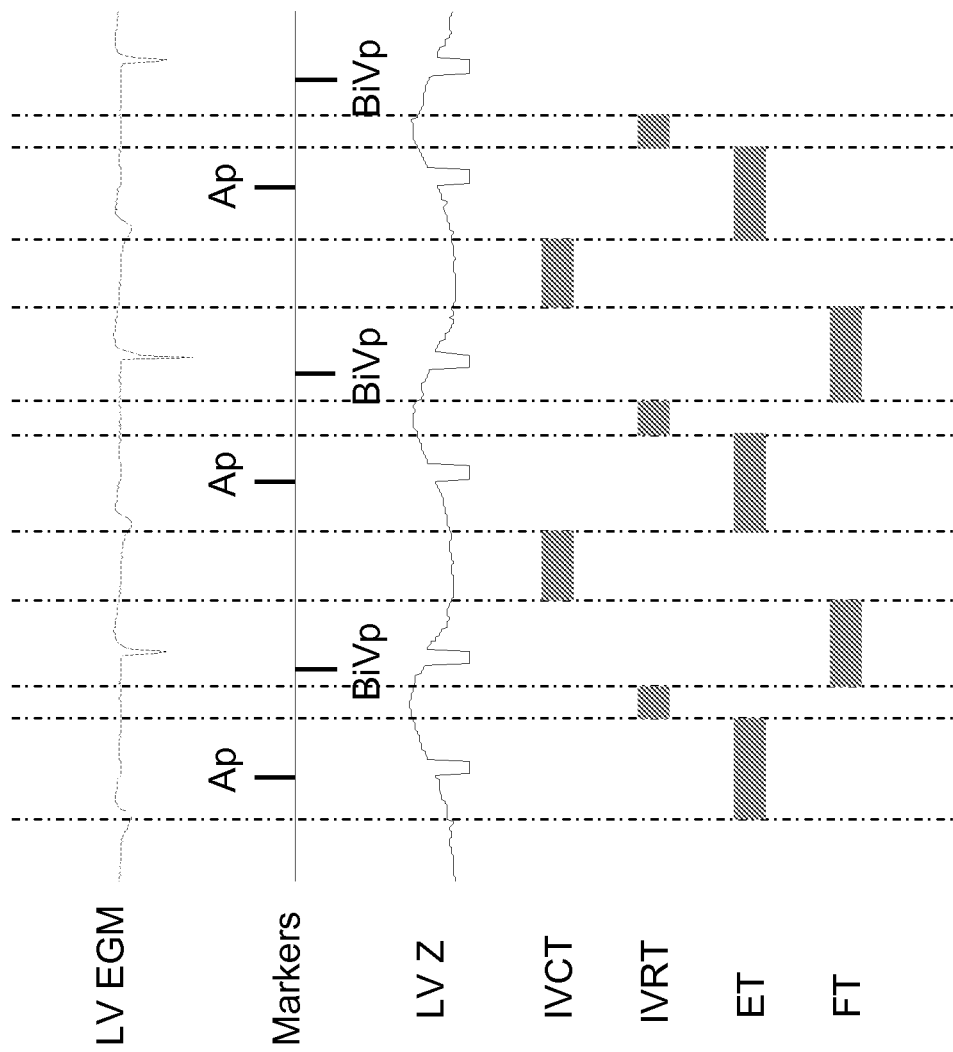

APPARATUS AND METHOD TO OPTIMIZE PACING PARAMETERS

This application claims the benefit of U.S. Provisional Patent Application No. 61/538,156 filed on 23 Sep. 2011, the specification of which is hereby incorporated herein by reference.

BACKGROUND OF THE INVENTION

1. Field of the Invention

At least one embodiment of the invention is related to a heart stimulator.

2. Description of the Related Art

Cardiac resynchronization therapy (CRT) is emerging as one of the primary treatments for patients with heart failure (HF). Numerous methods have been proposed and/or developed for optimal programming of the CRT devices, with particular focus on two timing parameters: atrio-ventricular delay (AVD), and the inter-ventricular delay (VVD).

Heart failure is a progressive disease that ultimately leads to ventricular dysfunction. Through the course of ventricular remodeling process, the ventricular geometry changes, which further causes conduction system abnormalities, for example, the inter- or intra-ventricular conduction delays. Consequently, contraction is no longer organized or synchronous between the left ventricle (LV) and right ventricle (RV), or within the LV and within RV or within the LV or within the RV or combinations thereof, leading to ventricular dyssynchrony.

The CRT is a proven technique for treating HF patients with cardiac dyssynchrony. In addition to conventional RV pacing, the LV is also paced by implanting a pacing lead through a transvenous approach via the coronary sinus (CS). By electrically stimulating the site of late ventricular activation, forcing the RV and LV to contract in a synchronized manner, the CRT can create a synchronized pumping of the ventricles, thus increasing the efficiency of ventricular contraction and improving the hemodynamics.

Nonetheless, clinical experience has shown that about one third of the CRT candidates are non-respondents, and the possible reasons may include inappropriate CS lead location, regional LV infarction, non-optimal pacing parameter settings, etc. Evidence has shown that optimizing pacing parameters, particularly the AVD and VVD, may change some CRT non-respondents to respondents. Even for the respondents, the AVD and VVD optimization may further improve the efficacy of the CRT.

The AVD optimization, which aims to maintain synchronized timing between the atria and ventricles, has been a focus of research since the early development of the dual-chamber pacemakers two decades ago. The introduction of CRT in the late 1990s has generated further interests in AVD optimization. In addition, it has brought a new challenge for VVD optimization, which aims to coordinate RV and LV contractions. Moreover, the AVD and VVD optimizations have been further complicated by other confounding factors, for example the pacing rate and the pacing mode.

Therefore a typical pacemaker is a heart stimulator that has at least one stimulation pulse generator to selectively generate stimulation pulse for delivery to at least two different chambers of a heart, said chambers include right and left atria and right and left ventricles. Said one stimulation pulse generator may be switchable in order to generate stimulation pulses for different chambers of the heart. In general, however, separate stimulation pulse generators will be provided for each heart chamber to be stimulated. The timing and triggering of stimulation pulses is typically controlled by a control unit. Time intervals to be timed by the control unit may inter alia include an atrioventricular time delay (AVD) between an atrial event and a ventricular event and/or an interventricular delay (VVD) between a right ventricular event and a left ventricular event.

State of the art pacemakers include means to optimize the atrioventricular and/or the interventricular delay based on a hemodynamic sensor information.

For AVD optimization the pacemaker provides for at least one atrial and one ventricular channel for pacing and/or sensing. For VVD optimization the pacemaker provides for pacing channels for both ventricles.

In a healthy heart, initiation of the cardiac cycle normally begins with depolarization of the sinoatrial (SA) node. This specialized structure is located in the upper portion of the right atrium wall and acts as a natural "pacemaker" of the heart. In a normal cardiac cycle and in response to the initiating SA depolarization, the right atrium contracts and forces the blood that has accumulated therein into the ventricle. The natural stimulus causing the right atrium to contract is conducted to right ventricle via the atrioventricular node (AV node) with a short, natural delay, the atrioventricular delay (AV-delay, AVD). Thus a short time after the right atrial contraction (a time sufficient to allow the bulk of the blood in the right atrium to flow through the one-way valve into the right ventricle), the right ventricle contracts, forcing the blood out of the right ventricle to the pulmonary artery. A typical time interval between depolarization of the right atrium and depolarization of the right ventricle might be 160 ms or 60 ms; a typical time interval between depolarization of the right ventricle and the next depolarization of the right atrium might be 800 ms. Thus, it is an right atrial depolarization (A), followed a relatively short time thereafter by a right ventricle depolarization (V), followed a relatively long time thereafter by the next right atrial depolarization, that produces the desired AV synchrony. Where AV synchrony exists, the heart functions very efficiently as a pump in delivering life-sustaining blood to body tissue; where AV synchrony is absent, the heart functions as an inefficient pump.

The term depolarization shall include the mechanical reaction of the tissue, the contraction, where appropriate.

Similarly, the left ventricle contracts in synchrony with right atrium and the right ventricle with a positive or negative time delay between a right ventricular contraction and a left ventricular contraction.

Also important is to address left-side AV synchrony (LA-LV).

A pacemaker generally shall induce a depolarization of a heart chamber by delivery of a stimulation pulse (pacing pulse) to said chamber when no natural (intrinsic) depolarization of said chamber occurs in due time. A depolarization of a heart chamber often is called "event". Since a depolarization may be an intrinsic depolarization, which can be sensed by an according sensing stage of a pacemaker, such event is called a sensed event. A depolarization due to delivery of a stimulation pulse is called a paced event. A sensed event in the atrium is called As, a paced atrial event is called Ap. Similarly, a sensed event in the ventricle is called Vs and a paced ventricular event is called Vp.

To mimic the natural behavior of a heart, a dual-chamber pacemaker provides for an AV-delay timer to provide for an adequate time delay (AV-delay, AVD) between a natural (intrinsic) or a stimulated (paced) right atrial depolarization and a right ventricular depolarization. In a similar way a biventricular pacemaker provides for an adequate time delay (VV-delay, VVD) between a right ventricular depolarization and a left ventricular depolarization.

The time delay for a left ventricular (stimulated, paced) contraction may be timed from a scheduled right ventricular contraction, which has not yet occurred or from a natural (intrinsic) or a stimulated (paced) right atrial contraction. In the latter case a left ventricular stimulation pulse is scheduled by a time interval AVD+VVD, where VVD may be a positive value (RV is paced before LV), or a negative value (LV is paced before RV), or zero (RV and LV are paced simultaneously).

To deal with possibly occurring natural (intrinsic) atrial or ventricular contractions, a demand pacemaker schedules a stimulation pulse for delivery at the end of the AV-delay or the VV-delay, respectively. The delivery of said stimulation pulse is inhibited, if a natural depolarization of the heart chamber to be stimulated is sensed within the respective time delay.

Ventricular pacing in one or both ventricles is required for patients with AV-block and for CHF patients that are indicated for cardiac resynchronization therapy (CRT). For patients with intact sinus rhythm or with effective atrial pacing it is beneficial to stimulate the ventricle(s) synchronous with the atrial activation, i.e., with a certain delay period after the atrial event. Standard AV-synchronous dual- or three-chamber implantable devices have a programmable AVD that can be adjusted by the physician. Several studies have shown the importance of individual AVD optimization to improve the cardiac output. Especially for CHF patients an optimization of the AVD is essential. As the pumping efficacy is impaired, the optimal timing of the ventricular stimulus in relation to the atrial event contributes significantly to the cardiac performance. If the AVD is too short, the ventricle contracts before it is completely filled by the atrial blood inflow. The active filling time is reduced. Hence the stroke volume and the cardiac output are reduced. If the AVD is too long, the ventricle contracts a while after the closure of the atrioventricular valve. Hence the passive filling time of the ventricle, i.e., the diastolic filling period during the myocardial relaxation before the atrial kick, is decreased. Also backflow of blood from the ventricle into the atrium, e.g., mitral regurgitation, is likely. Thus also in this case cardiac output (CO) is reduced. Similar to the heart rate, the optimal AVD also depends on the autonomic tone. If the sympathetic tone is high, e.g., during exercise, the optimal AVD is shortened compared to the resting value.

Patients with CHF and Left Bundle-Branch Block (LBBB), i.e., with intra- or inter-ventricular dyssynchrony expressed by a widened QRS complex in the electrogram may benefit from biventricular pacing. Pacing both ventricles simultaneously or with a certain VVD restores the synchrony of the ventricles and thus improves the hemodynamic performance. Also mitral regurgitation is reduced by biventricular pacing. Recent CRT pacing devices, implantable pulse generators (IPGs) or ICDs, offer a programmable VVD parameter. The delay time between the right ventricular (RV) and left ventricular (LV) stimulation can be programmed, usually approx. in the range −100 ms . . . +100 ms. The sign determines whether the RV or the LV is paced first. Zero ms, or 0 ms means simultaneous pacing of both ventricles. Also RV or LV-only pacing can be programmed. It has been found that the setting that results in optimal hemodynamics varies from patient to patient. The optimal value also depends on the individual position of the left ventricular pacing lead.

Some prior art pacemaker includes at least one impedance measuring stage being connected to electrodes or a connector for such electrodes to measure an intracardiac or intrathoracic impedance when in use.

For CRT optimization presently the following techniques are applied:

Conventionally, the AVD optimization in clinical practice has been achieved using echocardiographic techniques, particularly by measuring the pulse-wave Doppler signals of the mitral inflow. The most representative technique is the Ritter method, which estimates the optimal AVD based on the measured interval from the QRS onset to the end of A wave (active filling). Some variants of the Ritter method have also been proposed. Alternatively, the optimal AVD can be estimated, by maximizing the velocity time integral (VTI) of the aortic outflow or the mitral inflow. In addition, other Doppler-based methods for AVD optimization have also been explored, based on estimation of the cardiac output, the LV pressure derivative dP/dt, and the derived myocardial performance index (MPI), which is defined as the ratio of isovolumic contraction time plus the isovolumic relaxation time to the ejection time. Another non-invasive method for assessment of cardiac output is the thoracic impedance cardiography, which has been used for optimizing the AVD, and was found to give similar results as echocardiography. Recently, finger photoplethysmography as a simple method for non-invasive blood pressure monitoring, has been shown to be another attractive tool for optimizing AVD in CRT devices.

Alternatively, the AVD can be optimized based on hemodynamic indexes that are assumed to correlate to the stroke volume or cardiac output, such as the blood pressure or its temporal derivative, the ventricular volume (e.g., through chamber impedance measurement), the blood oxygen saturation, blood pH, blood temperature, etc.

The AVD and VVD can also be optimized based on some metrics derived from the surface ECG or intracardiac electrogram (IEGM) signal. For example, St. Jude Medical has developed the QuickOpt algorithm, which calculates the optimal AVD based on the measurement of P wave duration (PWD) from the surface ECG. An empirical formula was developed to calculate the optimal VVD based on the difference between left- and right-side AV conduction times and the inter-ventricular conduction times. In another example, Boston Scientific's EEHF+ algorithm calculates the optimal AVD based on patient's QRS width, the intrinsic AV interval, and the LV lead location and the pacing chamber. The optimal VVD is also empirically determined based on the difference between left- and right-side AV conduction times.

The importance of inter-atrial conduction time (IACT) on AVD optimization has long been recognized. The IACT is a critical interval in the interaction between left atrium (LA) emptying and LV filling. Programming AVD that is excessively longer than IACT will frequently cause diastolic mitral regurgitation, whereas programming AVD that is shorter than IACT will frequently cause P wave reversal or increased venous and pulmonary pressure because of atrial contraction against a closed mitral valve. The IACT can be approximate by the PWD, which could be measured on surface ECG or IEGM recorded from far-field sensing vectors. Studies have suggested that there may be a linear relationship between IACT and optimal AVD.

Studies have shown that the efficacy of CRT is related the site of LV pacing. While the selection of optimal LV pacing site is limited by the coronary venous anatomy, the introduction of multi-polar LV leads may offer more options to choose different LV pacing vectors that could potentially improve the cardiac hemodynamics.

Most non-invasive methods described above share two common disadvantages. First, AVD optimization can only be performed after initial implantation or during device follow-up, when specially trained technicians are present to operate the external devices for the measurement. Second, patients are required to remain sedated or in stable supine position during the entire optimization procedure, which is time-consuming. Therefore, on one hand, it adds to the already high cost of the CRT. On the other hand, the AVD optimized in such well-controlled environment is unlikely to be optimal in the ambulatory conditions.

The AVD optimization methods based on measurement of hemodynamic parameters usually require special sensors, and their technically reliability has not been proven.

The QuickOpt algorithm assumes there is a linear relationship between optimal AVD and the PWD. The EEHF+ algorithm assumes the optimal AVD is linearly related to QRS width and intrinsic AV interval. These assumptions do not consider the electrical-mechanical coupling of the myocardium, thus the AVD determined based on the timing of electrical events may not correspond to the optimal AV timing for the mechanical events of the heart. In fact, the recent Trials showed that the optimal AVD determined using these methods was not superior to empirically programmed AVD.

Typically, the IACT measurement requires special sensors or echo equipment. Moreover, previous studies failed to demonstrate sufficiently high correlation coefficient of the linear regression model between IACT and the optimal AVD. Therefore, significant deviance may exist between the model predicted optimal AVD and the truly optimal AVD. Similarly, this approach failed to consider the timing of mechanical events of the heart.

How to determine the optimal LV pacing site remains unclear. Although the general principle is to pace in the region with the most delayed activation and to avoid pacing in the infarct area, there is no proven guidance on how to achieve this.

BRIEF SUMMARY OF THE INVENTION

It is a feature of at least one embodiment of the invention to improve the efficacy of the cardiac resynchronization therapy through device A-V delay (AVD), V-V delay (VVD), and pacing site optimization.

A feature of at least one embodiment of the invention is achieved by a heart stimulator comprising a stimulation control unit, one or more stimulation units, a signal measurement unit, which is preferably an impedance measurement unit and a signal evaluation unit, which is preferably an impedance evaluation unit. The stimulation control unit is operatively connected to said one or more stimulation units to control timing of stimulation pulses by said one or more stimulation units. The signal measurement unit or impedance measurement unit is configured to determine an impedance signal reflecting intracardiac impedance. The signal evaluation unit or impedance evaluation unit is operatively connected to the signal measuring unit or impedance measurement unit and to the stimulation control unit and is configured to evaluate the signal or impedance signal so as to determine an isovolumic contraction time (IVCT), an isovolumic relaxation time (IVRT), an ejection time (ET) and a filling time (FT) from said signal or impedance signal. The stimulation control unit is further configured to control timing of stimulation pulses depending on a performance index derived from at least a sum of the isovolumic contraction time (IVCT) and the isovolumic relaxation time (IVRT) divided by a further cardiac cycle time period length of a respective heart cycle.

Furthermore the signal evaluation unit may at least be connected to the stimulation control unit, so that the stimulation control unit may receive input from the signal evaluation unit.

Preferably, the performance index is a cardiac performance index that reflects the sum of said isovolumic contraction time (IVCT) and said isovolumic relaxation time (IVRT) divided by a full heart cycle length including said isovolumic contraction time (IVCT), said isovolumic relaxation time (IVRT), said ejection time (ET) and said filling time (FT) of a respective heart cycle.

According to further preferred embodiments, the stimulation control unit is configured to apply a timing for triggering stimulation pulses that results in a minimum of said performance index.

Preferably, the impedance evaluation unit is configured to determine an isovolumic contraction time period by determining a nadir duration of the impedance signal. Likewise, the impedance evaluation unit can be configured to determine an isovolumic relaxation time period by determining the peak duration of the impedance signal. More specifically, the impedance evaluation unit can be configured to determine said nadir duration or said peak duration, respectively, by determining the first derivative of the impedance signal and finding those impedance samples with $abs(dZ/dt)<\Delta$, where $abs(\,)$ is the absolute function and $\Delta$ is a predefined positive value.

According to further preferred embodiments, the impedance evaluation unit is configured to determine the ejection time as the time interval between the end of isovolumic contraction time period and the beginning of next isovolumic relaxation time period. Likewise, the impedance evaluation unit is configured to determine the filling time as the time interval between the end of isovolumic relaxation time period and the beginning of next isovolumic contraction time period.

The impedance measurement unit is preferably configured to measure an impedance signal by injecting subthreshold biphasic current pulses between a right ventricular ring electrode tip and a left ventricular tip electrode, and by measuring a voltage between the right ventricular ring electrode and the a left ventricular ring electrode. Alternatively, the impedance measurement unit can be configured to measure an impedance signal by injecting subthreshold biphasic current pulses between a right atrial tip electrode and a left ventricular tip electrode, and by measuring a voltage between a right atrial ring electrode and a left ventricular ring electrode.

A feature of the invention is also achieved by a method for adjusting a timing of cardiac stimulation pulses, wherein the method comprises the steps of:

Measuring intracardiac impedance values determining from the intracardiac impedance values an isovolumic contraction time period and an isovolumic relaxation time period for a heart cycle determining a cardiac performance index reflecting a ratio between a) a sum of the isovolumic contraction time and the isovolumic relaxation time and b) a total heart cycle length adjusting timing of cardiac stimulation pulses so as to minimize the said cardiac performance index.

Adjusting of timing of cardiac stimulation pulses preferably includes adjusting an atrioventricular delay interval (AVD) and/or an interventricular delay interval (VVD).

Thus, an apparatus and method for optimizing pacing parameters is provided, including the A-V delay, V-V delay, and the pacing site, of implantable pacemakers or ICDs by minimizing the cardiac performance index derived from the intracardiac impedance measurement. The method allows frequent or periodic optimization of the pacing parameters under different load conditions, and does not require patient for a follow-up visit.

The optimal pacing configuration is achieved by minimizing the cardiac performance index (CPI) derived from the intracardiac impedance measurement. The CPI is defined as the ratio of the total isovolumic time to the cardiac cycle length, where the total isovolumic time is the sum of isovolumic contraction time and the isovolumic relaxation time. All of these time metrics can be automatically calculated by the device based on the measured intracardiac impedance signal.

BRIEF DESCRIPTION OF THE DRAWINGS

The above and other aspects, features and advantages of at least one embodiment of the invention will be more apparent from the following more particular description thereof, presented in conjunction with the following drawings wherein:

FIG. 7 shows a second example of measuring time intervals from the impedance signal.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1:
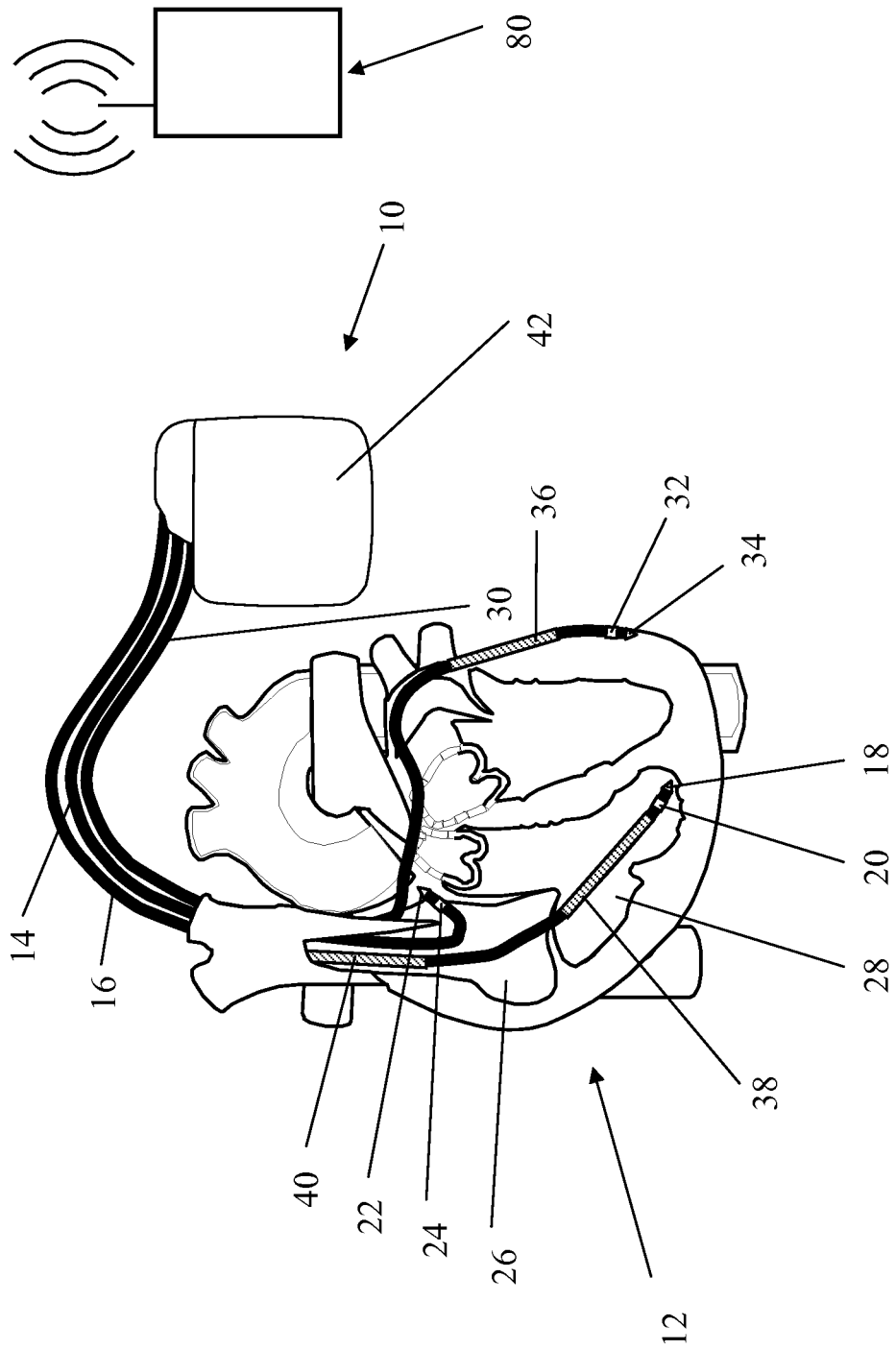
FIG. 1 shows a three chamber bi-ventricular implantable cardioverter/defibrillator (ICD).

In FIG. 1 the implantable medical device (also referred to as implantable cardiac device) is a three-chamber biventricular pacemaker and cardioverter/defibrillator 10 that is connected to pacing/sensing leads placed in a heart 12 is illustrated.

As shown in FIG. 1, the preferred embodiment is to couple the disclosed technology with an implantable bi-ventricular defibrillator.

The implantable medical device 10 is electrically coupled to heart 12 by way of leads 14, 16 and 30.

Lead 14 is a right atrial electrode lead that has a pair of right atrial electrodes 22 and 24 that are in contact with the right atria 26 of the heart 12.

Lead 16 is a right ventricular electrode lead that has a pair of ventricular stimulation and sensing electrodes 18 and 20 that are in contact with the right ventricle 28 of heart 12. Further, a ventricular defibrillation shock coil 38 and an atrial defibrillation shock coil 40 are arranged on lead 16.

Electrodes 22 and 18 are tip electrodes at the very distal end of leads 14 and 16, respectively. Electrode 22 is a right atrial tip electrode RA Tip and electrode 18 is a right ventricular tip electrode. Electrodes 24 and 20 are ring electrodes in close proximity but electrically isolated from the respective tip electrodes 22 and 18. Electrode 24 forms a right atrial ring electrode RA Ring and electrode 20 forms a right ventricular ring electrode RV Ring. Atrial cardioversion shock coil 40 is a coil electrode providing a relatively large geometric area when compared to the stimulation electrodes 18, 20, 22 and 24.

Lead 30 is a left ventricular electrode lead passing through the coronary sinus of heart 12 and having a left ventricular ring electrode LV RING 32 a left ventricular tip electrode LV TIP 34. Further, a left ventricular defibrillation shock coil 36 is arranged on lead 30.

Implantable medical device 10 has a case 42 made from electrically conductive material such as titanium that can serve as a large surface electrode IMD CASE.

The plurality of electrodes 18, 20, 22, 24, 32, 34, 36, 38 and 40 connected to implantable medical device 10 together with case 42 allow for a number of different electrode configurations for measuring intrathoracic and intracardiac impedance.

Figure 2:
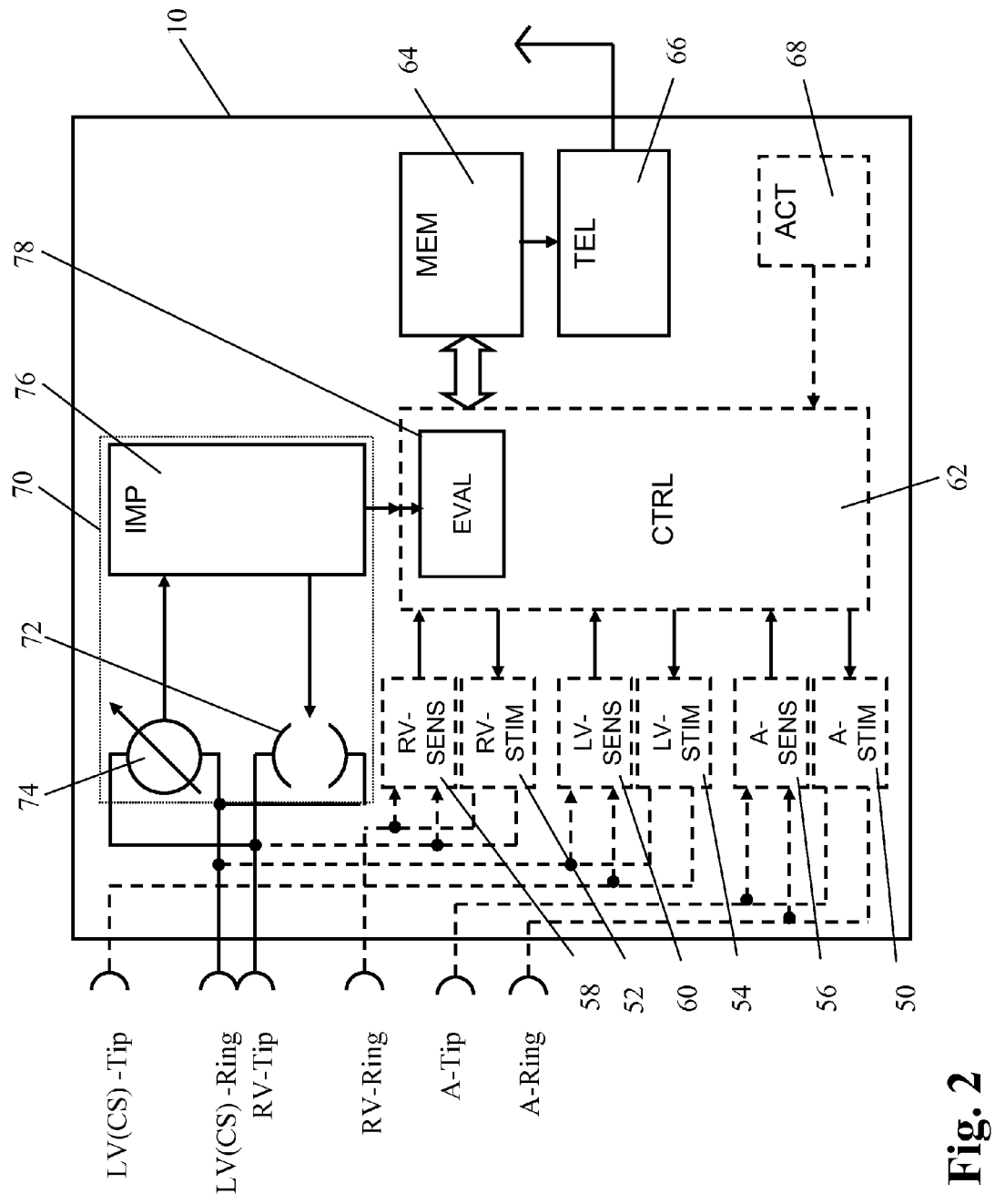
FIGS. 2 and 3 are schematic diagrams of two alternative embodiments of the device modules of the ICD of FIG. 1.
Figure 3:
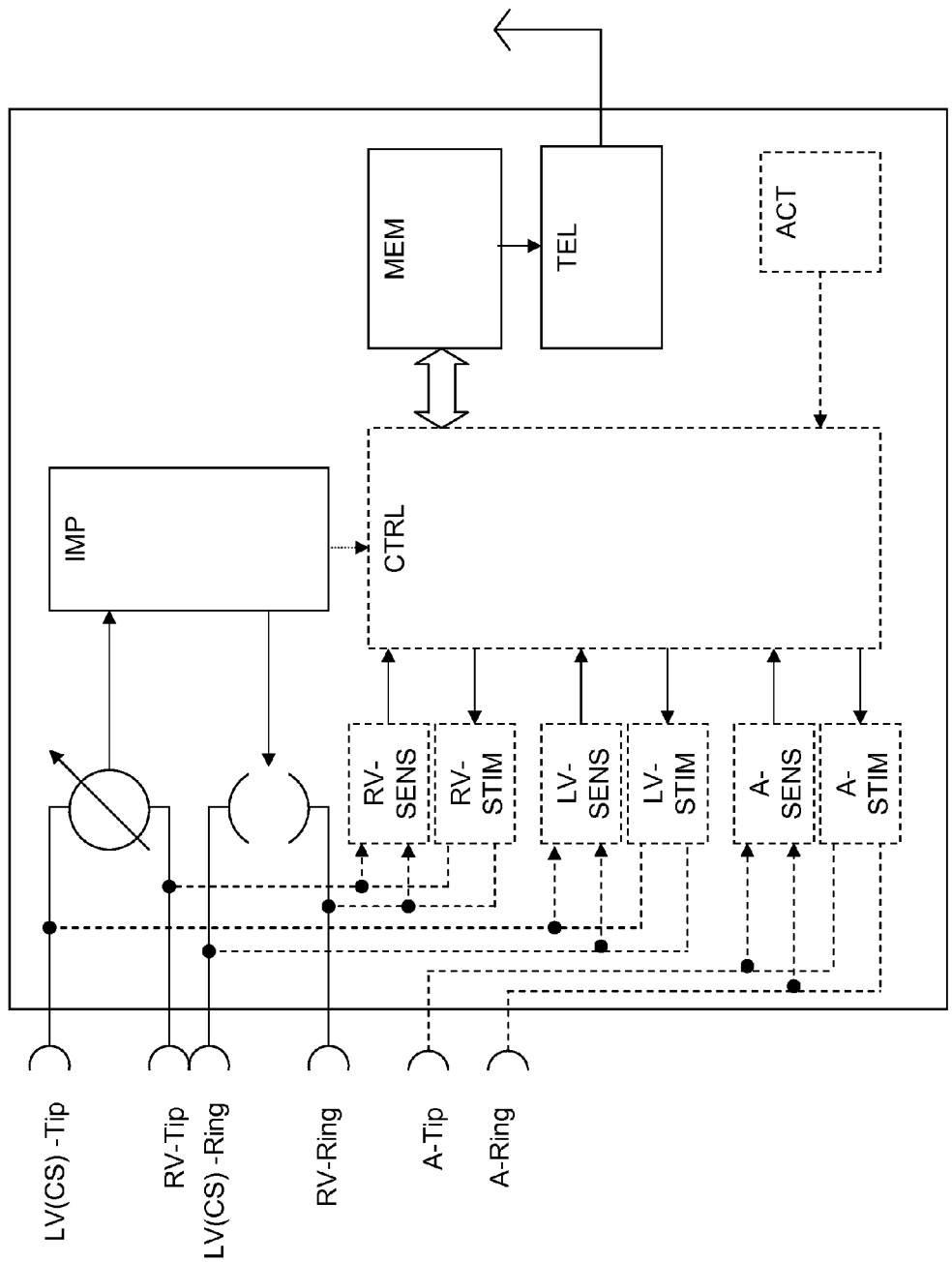

For intracardiac impedance measurements, injecting a forcing function from a right ventricular ring electrode to a left ventricular ring electrode and measuring a response function between the same electrodes (bipolar configuration; see FIG. 2) or, for instance, a right ventricular tip electrode and a left ventricular tip electrode (quadrupolar configuration; see FIG. 3).

Further possible electrode configurations for application of the forcing function and measurement of the response function become apparent from the following table:

| Polarity | Forcing contacts | Response contacts |
| --- | --- | --- |
| Tripolar | RV Ring to Case | RV Tip to Case |
| Tripolar | LV Ring to Case | LV Tip to Case |
| Bipolar | RV Coil to Case | RV Coil to Case |
| Bipolar | LV Coil to Case | LV Coil to Case |
| Quadrapolar #1 | LV Ring to RV Ring | LV Tip to RV Tip |
| Quadrapolar #2 | RV Ring to RV Tip | LV Ring to LV Tip |
| Tripolar | RV Ring to LV Ring | RV Tip to LV Ring |
| Tripolar | RV Ring to LV Tip | RV Tip to LV Tip |
| Tripolar | LV Ring to RV Ring | LV Tip to RV Ring |
| Tripolar | LV Ring to RV Tip | LV Tip to RV Tip |
| Bipolar | RV Ring to LV Ring | RV Ring to LV Ring |
| Bipolar | RV Tip to LV Tip | RV Tip to LV Tip |
| Bipolar | RV Ring to LV Tip | RV Ring to LV Tip |
| Bipolar | RV Tip to LV Ring | RV Tip to LV Ring |

Referring to FIG. 2 illustrating a simplified block diagram of an implantable medical device 10. During operation of the pacemaker leads 14, 16 and 30 are connected to respective output/input terminals of pacemaker 10 as indicated in FIG. 2 and carry stimulating pulses to the tip electrodes 18, 22 and 34 from a right atrial stimulation pulse generator A-STIM 50, a right ventricular pulse generator RV-STIM 52 and a left ventricular pulse generator LV-STIM 54, respectively. Further, electrical signals from the right atrium are carried from the electrode pair 22 and 24, through the lead 14, to the input terminal of a right atrial channel sensing stage A-SENS 56; and electrical signals from the right ventricle are carried from the electrode pair 18 and 20, through the lead 16, to the input terminal of a right ventricular sensing stage RV-SENS 58. Likewise electrical signals from the left ventricle are carried from the electrode pair 32 and 34, through the lead 30, to the input terminal of a left ventricular sensing stage LV-SENS 60.

Controlling the implantable medical device 10 is a control unit CTRL 62 that is connected to sensing stages A-SENS 56, RV-SENS 58 and LV-SENS 60 and to stimulation pulse generators A-STIM 50, RV-STIM 52 and LV-STIM 54. Control unit CTRL 62 receives the output signals from the atrial sensing stage A-SENS 56, from the right ventricular sensing stage RV-SENS 58 and from the left ventricular sensing stage LV-SENS 60. The output signals of sensing stages A-SENS 56, RV-SENS 58 and LV-SENS 60 are generated each time that a P-wave representing an intrinsic atrial event or an R-wave representing an intrinsic ventricular event, respectively, is sensed within the heart 12. An As-signal is generated, when the atrial sensing stage A-SENS 56 detects a P-wave and a RVs-signal is generated, when the right ventricular sensing stage RV-SENS 58 detects an R-wave.

These sense events are used by control unit CTRL 62 as fiducial points of the respective intracardiac electrograms picked up by the sensing stages A-SENS 56, RV-SENS 58 and LV-SENS 60, respectively.

Control unit CTRL 62 also generates trigger signals that are sent to the atrial stimulation pulse generator A-STIM 50, the right ventricular stimulation pulse generator RV-STIM 52 and the left ventricular stimulation pulse generator LV-STIM 54, respectively. These trigger signals are generated each time that a stimulation pulse is to be generated by the respective pulse generator A-STIM 50, RV-STIM 52 or LV-STIM 54. The atrial trigger signal is referred to simply as the "A-pulse", and the ventricular trigger signal is referred to as the "RV-pulse" or the "LV-pulse", respectively. During the time that either an atrial stimulation pulse or ventricular stimulation pulse is being delivered to the heart, the corresponding sensing stage, A-SENS 56, RV-SENS 58 and/or LV-SENS 60, is typically disabled by way of a blanking signal presented to these amplifiers from the control unit CTRL 62, respectively. This blanking action prevents the sensing stages A-SENS 56, RV-SENS 58 and LV-SENS 60 from becoming saturated from the relatively large stimulation pulses that are present at their input terminals during this time. This blanking action also helps prevent residual electrical signals present in the muscle tissue as a result of a stimulation pulse delivered from pacemaker 10 from being interpreted as P-waves or R-waves.

Furthermore, atrial sense events As recorded shortly after delivery of a ventricular stimulation pulses during a preset time interval called post ventricular atrial refractory period (PVARP) are generally recorded as atrial refractory sense event Ars but ignored.

Control unit CTRL 62 comprises circuitry for timing ventricular and/or atrial stimulation pulses according to an adequate stimulation rate that can be adapted to a patient's hemodynamic need as pointed out below.

Still referring to FIG. 2, the implantable medical device 10 includes a memory circuit MEM 64 that is coupled to the control unit CTRL 62 over a suitable data/address bus ADR. This memory circuit MEM 64 allows certain control parameters, used by the control unit CTRL 62 in controlling the operation of the implantable medical device 10, to be programmably stored and modified, as required, in order to customize the implantable medical device's operation to suit the needs of a particular patient. Such data includes the basic timing intervals used during operation of the pacemaker 10 and AV delay values and hysteresis AV delay values in particular.

Further, data sensed during the operation of the implantable medical device 10 may be stored in the memory MEM 64 for later retrieval and analysis.

A telemetry circuit TEL 66 is further included in the implantable medical device 10. This telemetry circuit TEL 6 is connected to the control unit CTRL 62 by way of a suitable command/data bus. Telemetry circuit TEL 66 allows for wireless data exchange between the implantable medical device 10 and some remote programming or analyzing device, which can be part of a centralized service center serving multiple pacemakers.

The implantable medical device 10 in FIG. 2 is referred to as a three chamber pacemaker/cardioverter/defibrillator because it interfaces with the right atrium 26, the right ventricle 28 and the left ventricle of the heart 12. Those portions of the pacemaker 10 that interface with the right atrium, e.g., the lead 14, the P-wave sensing stage A-SENSE 56, the atrial stimulation pulse generator A-STIM 50 and corresponding portions of the control unit CTRL 62, are commonly referred to as the atrial channel. Similarly, those portions of the pacemaker 10 that interface with the right ventricle 28, e.g., the lead 16, the R-wave sensing stage RV-SENSE 58, the ventricular stimulation pulse generator RV-STIM 52, and corresponding portions of the control unit CTRL 62, are commonly referred to as the ventricular channel.

In order to be able to detect periods of physical activity of a patient indicating that the patient is awake and in order to allow rate adaptive pacing in a DDDR or a DDIR mode, the pacemaker 10 further includes a physiological sensor ACT 68 that is connected to the control unit CTRL 62 of the pacemaker 10. While this sensor ACT 68 is illustrated in FIG. 2 as being included within the pacemaker 10, it is to be understood that the sensor may also be external to the implantable medical device 10, yet still be implanted within or carried by the patient. A common type of sensor is an accelerometer, such as a piezoelectric crystal, mounted to the case of the pacemaker. Other types of physiologic sensors are also known, such as sensors that sense the oxygen content of blood, respiration rate, blood pH, intracardiac impedance changes, and the like. The type of sensor used is not critical to the present invention. Any sensor capable of sensing some physiological parameter relatable to physical activity of a patient can be used. Such sensors are commonly used with "rate-responsive" pacemakers in order to adjust the rate of the pacemaker in a manner that tracks the physiological needs of the patient. The output of sensor 68 represents an activity level.

By means of the output signal of activity sensor 68 the control unit 62 is able to assign each intrinsic heart rate to an activity thus enabling collection of intrinsic heart rate value for a patient's state of rest and a patient's state of exercise separately.

The control unit CTRL 62 is adapted to determine an adequate heart rate or stimulation rate in any manner known as such.

For impedance measurement, an impedance determination unit 70 is provided. Impedance determination unit 70 comprises a constant current source 72 that is connected or can be connected to electrodes for intracorporeal placement as shown in FIG. 1. In order to allow for a plurality of impedance measurement electrode configurations, preferably some means of switching is provided between the constant current source 72 and the electrode terminals of the implantable medical device 10. The switch is not shown in FIG. 2. Rather, particular impedance measurement configurations are shown as examples.

Similarly, a voltage measuring unit 74 for measuring a voltage corresponding to a current fed through a body by said constant current source is provided and can be connected to a number of electrodes although a switch for switching between these configurations is not shown in FIG. 2.

As an alternative to constant current source 72 a constant voltage source can be provided to generate the forcing function. Then, the measuring unit will be adapted to measure a current strength of a current fed through a body by said constant voltage source.

Both, constant current source 72 and voltage measurement unit 74, are connected to an impedance value determination unit 76 that is adapted to determine an impedance value for each measuring current pulse delivered by the constant current source 72.

Further, an evaluation unit 78 is provided either as a separate unit or as part of control unit CTRL 62 as depicted in FIG. 2. The evaluation unit 78 is connected to the impedance measurement unit 70 and is adapted to evaluate a sequence of consecutive impedance values determined by said impedance measurement unit. The evaluation unit 78 comprises a signal generator module (not shown) to construct the intracardiac impedance or conductance signal reflecting the time course of the impedance measurement unit's output signal and its derivative.

The evaluation unit 78 further comprises a filter module (not shown) to filter the intracardiac impedance signal.

The evaluation unit 78 is further connected to the right ventricular stimulation stage RV-STIM 52 and the right ventricular sensing stage RV-SENS 58 in order to receive signals representing cardiac events, namely right ventricular stimulation events RVp or right ventricular sense events RVs, respectively.

The constant current source 72 has its two poles connected to different connectors for different electrodes as for example the right ventricular ring electrode and the left ventricular ring electrode (FIG. 2) or the left ventricular tip electrode and the right ventricular tip electrode (FIG. 3). The voltage measuring unit 74 has two poles connected to, for example, a connector for the left ventricular ring electrode and the right ventricular ring electrode (FIG. 2) or the left ventricular ring electrode and the right ventricular ring electrode (FIG. 3). Thus, a bipolar or a quadrupolar impedance measurement configuration is established.

Impedance measurement is carried out by injecting a constant current and sampling the resulting voltage.

The measuring current is preferably pulsed. Typically, the measuring current will feature biphasic pulses wherein two constant current pulses of opposite polarity form one pulse package. Two consecutive pulse packages between two consecutive pulse packages a time gap is provided, which is significantly longer than the duration of one pulse package. The constant current pulses within one pulse package are each of the same intensity and of same duration. They only have different polarities. The typical value for the intensity of the constant current pulses is between 50 µA and 600 µA. The typical pulse duration of a single constant current pulse is about 15 µs.

The time gap between each two consecutive pulse packages may be 500 times longer than the duration of one constant current pulse. The two constant current pulses of opposite polarity within one pulse package may not follow immediately each other but may have a time gap there between. This time gap however, will be very short compared to the time gap between two consecutive pulse packages. Furthermore, consecutive pulse packages may be face alternating such that a first pulse package for example will begin with a positive constant current pulse whereas the following pulse package will begin with a negative constant current pulse and end with a positive constant current pulse.

Figures 4A, 4B:
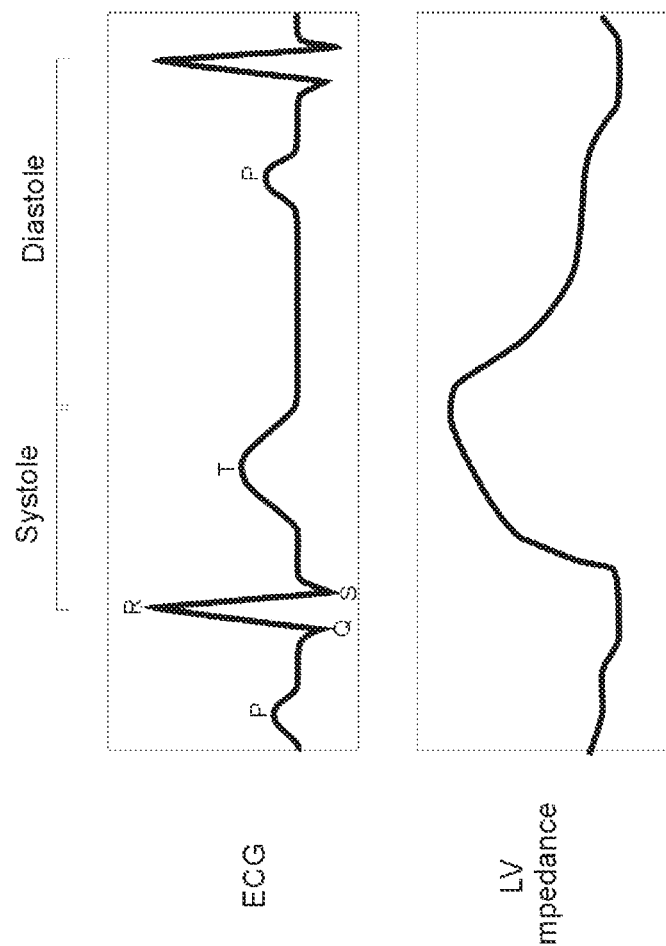
FIG. 4A shows an outline of an electrocardiogram over somewhat more than one cardiac cycle.
FIG. 4B shows a typical curve of the intracardial impedance in synoptic illustration to the curve of the electrocardiogram in FIG. 4A.

In FIG. 4B a typical time course of the left ventricular impedance Z is depicted. FIG. 4B shows a typical electrocardiogram. When the left ventricle has its smallest volume at the end of the systole (contraction of the ventricle) the impedance Z has a maximum. The time course of the impedance inversely reflects the time course left ventricular volume.

The main purpose of the sensing stages 56, 58 and 60 is to detect a natural (intrinsic) contraction of the respective heart chamber in order to generate a sense event signal like an atrial sense event As, a right ventricular sense event RVs and a left ventricular sense event LVs. These sense events are processed by the control unit CTRL 62 in order to inhibit a delivery of a stimulation pulse when the pacemaker is operating in a demand mode or in order to determine a time interval between an atrial event and a point of time, when the course of the left ventricular intracardiac impedance reaches its minimum value, see below.

Another type of event to be processed by the control unit CTRL 62 would be the delivery of a stimulation pulse to a respective heart chamber. Delivery of a stimulation pulse causes a paced event such as an atrial paced event Ap, a right ventricular paced event RVp and a left ventricular paced event LVp.

According to a preferred embodiment of the invention, different optimal time delays for different stimulation (pacing) rates and thus for different states of metabolic demand are determined. Therefore, memory MEM 64 is provided and connected to control unit CTRL 62 which is adapted to store optimal time delays such as optimal AV-delays AVD_opt and optimal VV-delays VVD_opt for different states of exertion.

Memory MEM 64 also serves for storing transient values for a measured impedance (end systolic impedance ESZ) and tested time delays associated therewith as disclosed in more detail further below.

Figure 6:
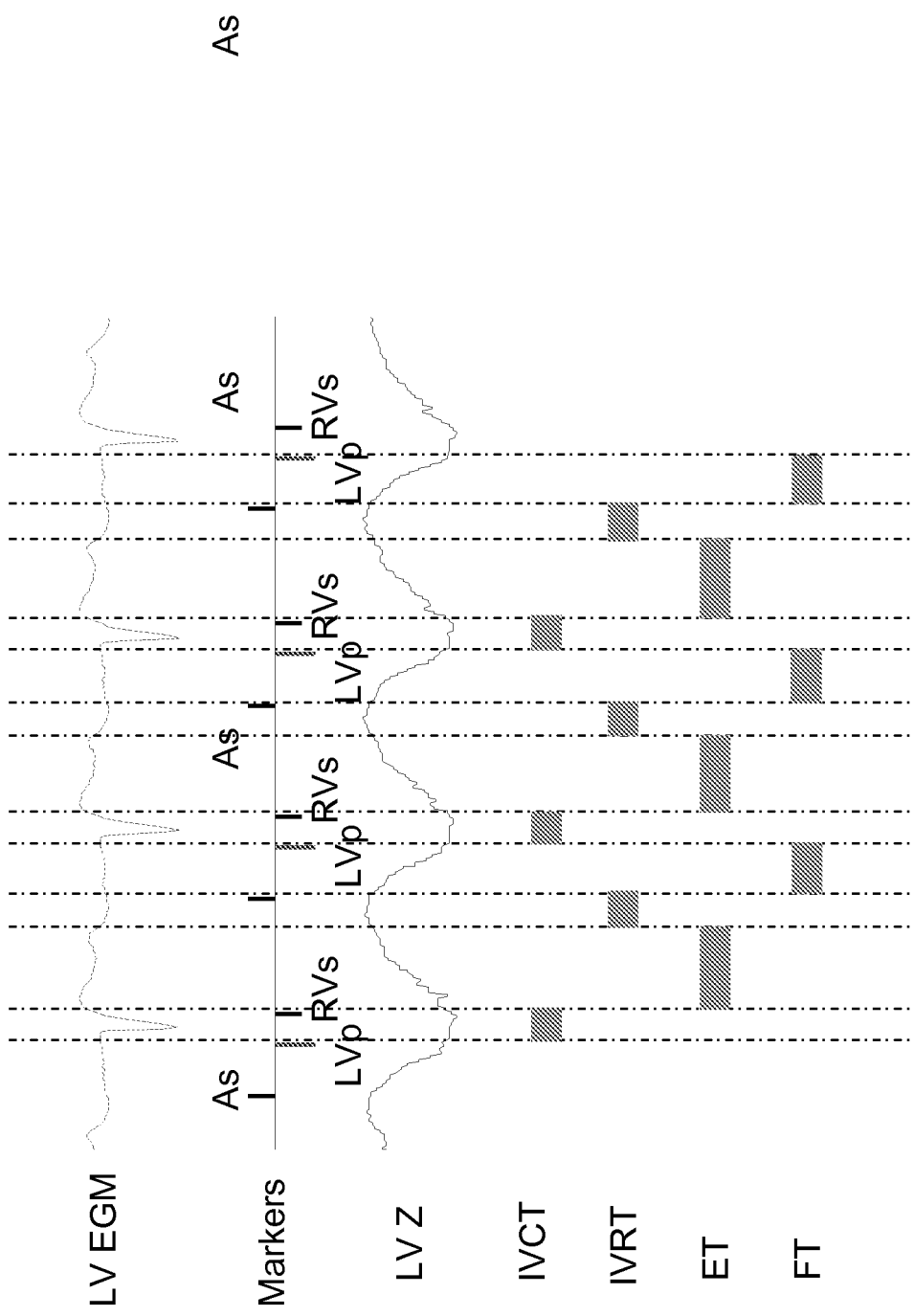
FIG. 6 shows a first example of measuring time intervals from the impedance signal.

The evaluation unit EVAL 78 is adapted to determine from the time course of the impedance value time periods for each cardiac cycle that correspond to a filling period, an isovolumic contraction period, an ejection period and an isovolumic relaxation period, respectively, as further illustrated by FIGS. 6 and 7.

When in use, the implantable cardiac device measures the intracardiac impedance (Z), from which a plural of timing intervals are derived that characterize different phases of the cardiac contraction, such as the isovolumic contraction time (IVCT), isovolumic relaxation time (IVRT), ejection time (ET), and filling time (FT). The total isovolumic time (TIVT) is the sum of IVCT and IVRT, and the cardiac cycle length (CL) is the sum of IVCT, IVRT, ET, and FT. At least three metrics could be derived from these timing intervals. The Systolic Performance Index (SPI) is defined as the ratio of TIVT to ET. The Diastolic Performance Index (DPI) is defined as the ratio of TIVT to FT. The Cardiac Performance Index (CPI) is defined as the ratio of TIVT to CL. According to a preferred embodiment, the pacing parameters, including the A-V delay (AVD), V-V delay (VVD), and the pacing site (for example, to choose the optimal LV pacing vector using a multi-polar LV electrodes), are considered optimal when the setting results in minimum CPI. In another embodiment, the pacing parameters are considered to be optimal when the setting results in minimum SPI or minimum DPI.

The intracardiac impedance (Z) can be measured in various means. Preferably, the impedance vector spans across the left ventricle (LV) to reflect the volume change of the LV chamber.

Figure 5A:
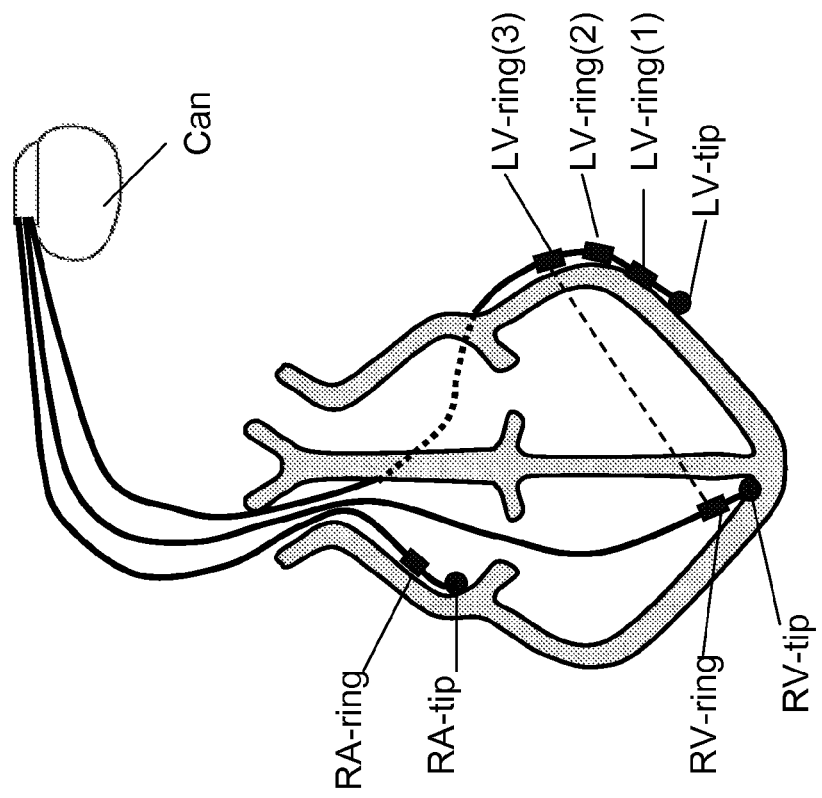
FIGS. 5A and 5B show exemplary configurations for measuring intracardiac impedance.
Figure 5B:
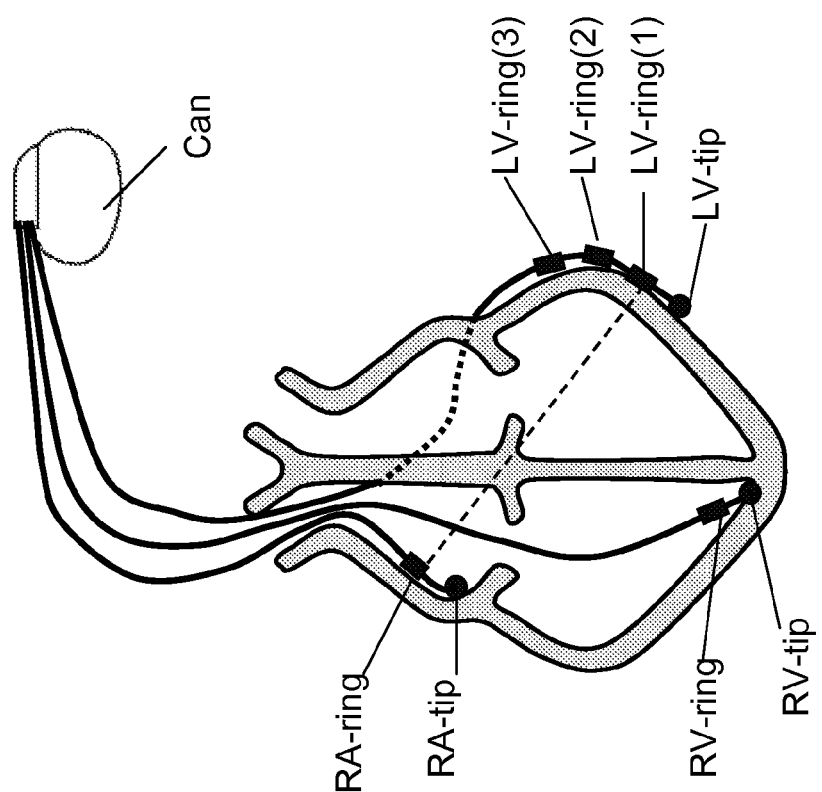

FIGS. 5A-B shows two typical examples. In FIG. 5A, subthreshold biphasic current pulses are injected between the RA tip and LV tip electrodes, and the voltage is measured between the RA ring and one of the LV ring electrodes. The ratio of the measured voltage to the injected current then approximately represents the impedance between the distal end of the RA lead and the distal end of the LV lead. In FIG. 5B, subthreshold biphasic current pulses are injected between the RV tip and LV tip electrodes, and the voltage is measured between the RV ring and one of the LV ring electrodes. The ratio of the measured voltage to the injected current then approximately represents the impedance between the distal end of the RV lead and the distal end of the LV lead. In both examples, the impedance vector passes through the LV chamber, thus the measured impedance is affected by the blood volume change of the LV. Clearly, it should be understood that LV impedance could also be measured by other electrode configurations, and they are considered within the scope of this invention.

In this respect, it is to be noted, that besides AV/VV delay optimization, the disclosed concept is also applicable to pacing site optimization. Specifically, when a multi-polar LV lead is used (as in FIGS. 5A and 5B), the LV pacing site can be optimized by choosing the LV electrode (thus the LV pacing vector) that minimizes the proposed cardiac performance index (CPI). Due to the anatomic constraint of the coronary venous, conventional unipolar or bipolar LV lead may not be able to pace the myocardial region with the most delayed activation or avoid the infarct area.

Employing multipolar LV lead, in conjunction with the proposed optimization method, it is feasible to select the optimal LV pacing site that improves the intraventricular synchrony and maximizes the cardiac performance.

Generally, a decrease in the Z signal implies increase in blood volume along the measurement vector, for example, during ventricular filling, whereas an increase in the Z signal correlates to decrease in blood volume along the measurement vector, for example, during ventricular systole. Therefore, from the device measured impedance curve, different phases of the cardiac cycle can be identified on a beat-to-beat basis, as illustrated in FIG. 6 and FIG. 7.

For each cardiac cycle, four time intervals IVCT, IVRT, ET, and FT can be measured from the LV Z signal. The IVCT can be measured as the nadir duration of the Z signal, and the IVRT can be measured as the peak duration of the Z signal. The peak duration and nadir duration can be measured from the first derivative of the Z signal, for example, to find the impedance samples with abs(dZ/dt)<A, where abs( ) is the absolute function and A is a predefined positive value. The time interval between the end of IVCT and the beginning of next IVRT is the ET, and the time interval between the end of IVRT and the beginning of next IVCT is the FT.

FIG. 6 shows a segment of data recorded by a three-chamber pacemaker, including LV electrogram (EGM), event markers, LV impedance (Z), and the measured time intervals. The heart rhythm is As-LVp-RVs, that is, intrinsic atrial sense (As) followed by LV only pacing (LVp) and RV sense (RVs). The As-LVp delay is set to 100 ms. It is clear that both IVCT and IVRT are much shorter compared to ET and FT. In other words, heart function is efficient because it spends longer time to pump blood during ejection phase and fill the chamber during relaxation phase than the isovolumic phases.

FIG. 7 shows another segment of data recorded by a CRT device, including LV electrogram (EGM), event markers, LV impedance (Z), and the measured time intervals. The heart rhythm is Ap-BiVp, that is, atrial pacing (Ap) followed by simultaneous biventricular pacing (BiVp). The Ap-BiVp delay is set to 200 ms and VVD is set to 0 ms. The downward spikes in the LV Z waveform are due to post-pace blanking, and these artifacts could be removed or filtered out by the device software prior to impedance analysis. It is clear that although the IVRT is still relatively short, the IVCT is markedly prolonged. In other words, heart function is less efficient because it spends more time in isovolumic phases, thus having less time available for pumping blood during the ejection phase and filling the ventricles during the relaxation phase.

To quantitatively measure the efficiency of heart function, the following three metrics can be defined based on the measured time intervals:

$$SPI=(IVCT+IVRT)/ET$$

$$DPI=(IVCT+IVRT)/FT$$

$$CPI=(IVCT+IVRT)/(IVCT+IVRT+ET+FT)$$

The systolic performance index (SPI) is the ratio of total isovolumic time (TIVT) to ET, and it measures the systolic performance of the heart. Higher SPI indicates lower systolic efficiency and lower SPI indicates higher systolic performance. The diastolic performance index (DPI) is the ratio of TIVT to FT, and it measures the diastolic performance of the heart. Higher DPI indicates lower diastolic efficiency and lower DPI indicates higher diastolic performance. The cardiac performance index (CPI) is the ratio of TIVT to the cardiac cycle length (CL), which is the sum of IVCT, IVRT, ET, and FT. The CPI measures the overall performance of the heart, taking into consideration of both systolic and diastolic functions. Higher CPI corresponds to lower cardiac efficiency and lower CPI corresponds to higher cardiac performance.

According to at least one embodiment of the invention, the LV impedance signal is recorded by varying different pacing parameters, including the A-V delay (AVD), V-V delay (VVD), and the pacing site (e.g. the selection of pacing electrode in the multipolar LV lead). For each configuration, the time intervals (IVCT, IVRT, ET, and FT) are measured by the device, and the SPI, DPI and CPI are respectively calculated. According to a preferred embodiment, the optimal pacing parameters are determined when they result in the minimum CPI (i.e. maximum cardiac efficiency). In another embodiment, the pacing parameters are considered to be optimal when the setting results in minimum SPI (i.e. maximum systolic efficiency) or minimum DPI (i.e. maximum diastolic efficiency).

An alternative definition of CPI is:

$$CPI=(IVCT+IVRT)/(ET+FT).$$

Compared to the original definition CPI=(IVCT+IVRT)/(IVCT+IVRT+ET+FT), the difference is the removal of (IVCT+IVRT) from the denominator. Although these two definitions will give different CPI values, they will both lead to the same optimal CRT configuration (i.e. corresponding to the minimal CPI). The concept remains the same, that is, to minimize the total isovolumic time adjusted for both systolic interval and diastolic interval.

The heart stimulator and the method described herein provide a means of optimizing pacing parameters based on mechanical time intervals derived from the impedance signal. The optimization scheme can be automated in an implantable cardiac device. The optimization strategy can be individually tailored to optimize the systolic function, or diastolic function, or the overall cardiac function. It allows frequent or periodic optimization of the pacing parameters under different load conditions, and does not require patient for a follow-up visit.

It is to be noted, that, while the method to optimize CPI is described based on a typical embodiment of intracardiac impedance measurement. The scope of the invention can be extended to other embodiments that measure the corresponding cardiac intervals, such as using intracardiac pressure sensor, acoustic sensor (to detect heart valve opening/closing), the intracardiac accelerometer (to detect endocardial acceleration/deceleration), etc. It can even be used in non-invasive close-loop CRT optimization systems based on echocardiography, finger plythysmography, etc.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A heart stimulator comprising
a stimulation control unit;
one or more stimulation units;
a signal measurement unit;
a signal evaluation unit;
said one or more stimulation units configured to generate stimulation pulses and to deliver a stimulation pulse to a heart when triggered by said stimulation control unit;
said stimulation control unit operatively connected to said one or more stimulation units to control pacing site and/or timing of said stimulation pulses by said one or more stimulation units;
said signal measurement unit configured to determine a signal that represents mechanical heart action of said heart;
said signal evaluation unit operatively connected to said signal measurement unit and to said stimulation control unit and configured to evaluate said signal that represents mechanical heart action to determine an isovolumic contraction time (IVCT), an isovolumic relaxation time (IVRT), an ejection time (ET) and a filling time (FT) from said signal that represents mechanical heart action; and,
said stimulation control unit further configured to control the pacing site and/or the timing of stimulation pulses based on a performance index derived from at least a sum of said isovolumic contraction time (IVCT) and said isovolumic relaxation time (IVRT) divided by a further cardiac cycle time period length of a respective heart cycle;
wherein said signal measurement unit is an impedance measurement unit and said signal evaluation unit is an impedance evaluation unit;
wherein said impedance measurement unit is configured to determine an impedance signal that represents intracardiac impedance; and,
wherein said impedance evaluation unit is configured to evaluate said impedance signal to determine said isovolumic contraction time (IVCT), said isovolumic relaxation time (IVRT), said ejection time (ET) and said filling time (FT) from said impedance signal.

2. The heart stimulation according to claim 1, wherein said performance index is a cardiac performance index that represents a sum of said isovolumic contraction time (IVCT) and said isovolumic relaxation time (IVRT) divided by a full heart cycle length including said isovolumic contraction time (IVCT), said isovolumic relaxation time (IVRT), said ejection time (ET) and said filling time (FT) of a respective heart cycle.

3. The heart stimulation according to claim 1, wherein said performance index is a cardiac performance index that represents a sum of said isovolumic contraction time (IVCT) and said isovolumic relaxation time (IVRT) divided by a sum of the filling time (FT) and the ejection time (ET).

4. The heart stimulator according to claim 1, wherein said stimulation control unit is configured to apply the timing of stimulation pulses that results in a minimum of said performance index.

5. The heart stimulator according to claim 1, wherein said impedance evaluation unit is configured to determine the isovolumic contraction time through determination of a nadir duration of the impedance signal.

6. The heart stimulator according to claim 1, wherein said impedance evaluation unit is configured to determine the isovolumic relaxation time period through determination of a peak duration of the impedance signal.

7. The heart stimulator according to claim 5, wherein said impedance evaluation unit is further configured to determine the isovolumic relaxation time period through determination of a peak duration of the impedance signal and wherein said impedance evaluation unit is configured to determine said nadir duration or said peak duration, respectively, through determination of a first derivative of the impedance signal through a search of impedance samples with $abs(dZ/dt)<\Delta$, where $abs( )$ is an absolute function and $\Delta$ is a predefined positive value.

8. The heart stimulator according to claim 1, wherein said impedance evaluation unit is configured to determine the ejection time as a time interval between an end of the isovolumic contraction time and a beginning of a next isovolumic relaxation time.

9. The heart stimulator according to claim 1, wherein said impedance evaluation unit is configured to determine a filling time as a time interval between an end of the isovolumic relaxation time and a beginning of a next isovolumic contraction time.

10. The heart stimulator according to claim 1, wherein said impedance measurement unit is configured to measure an impedance signal through injection of subthreshold biphasic current pulses between a right ventricular ring electrode tip and a left ventricular tip electrode, and through measurement of a voltage between the right ventricular ring electrode and a left ventricular ring electrode.

11. The heart stimulator according to claim 1, wherein said impedance measurement unit is configured to measure an impedance signal through injection of subthreshold biphasic current pulses between a right atrial tip electrode and a left ventricular tip electrode, and through measurement of a voltage between a right atrial ring electrode and a left ventricular ring electrode.

12. A method for adjusting pacing parameters of a heart stimulator and adjusting timing of cardiac stimulation pulses, said method comprising the steps of:
determining an impedance signal that represents intracardiac impedance using an impedance measurement unit of a heart stimulator;
measuring intracardiac impedance values from said impedance signal using an impedance evaluation unit of said heart stimulator;
evaluating said impedance signal and determining from said intracardiac impedance values of said impedance signal an isovolumic contraction time period, an ejection time period, a filling time period, and an isovolumic relaxation time period for a heart cycle using said impedance evaluation unit;
determining a cardiac performance index that represents a ratio between a sum of said isovolumic contraction time and said isovolumic relaxation time, and a total heart cycle length; and,
adjusting timing of cardiac stimulation pulses to minimize said cardiac performance index.

13. The method according to claim 12, wherein the pacing parameters to be adjusted include timing of cardiac stimulation pulses, and wherein the timing of cardiac stimulation pulses is adjusted to minimize said cardiac performance index.

14. The method of claim 13, wherein said adjusting of timing of cardiac stimulation pulses includes adjusting an atrioventricular delay interval (AVD) and/or an interventricular delay interval (VVD).

15. The method according to claim 12, wherein the pacing parameters to be adjusted include a pacing site for delivery of cardiac stimulation pulses, and wherein the pacing site is adjusted to minimize said cardiac performance index.

16. The method according to claim 12, wherein said total heart cycle length is a sum of said isovolumic contraction time, said isovolumic relaxation time, said ejection time and said filling time.

* * * * *